United States Patent [19]

Byer

[11] 4,386,854

[45] Jun. 7, 1983

[54] METHOD AND MEANS FOR OPTICALLY GENERATING SIGNALS FOR USE IN MONITORING AN ENVIRONMENT USING TOMOGRAPHIC TECHNIQUES

[75] Inventor: Robert L. Byer, Stanford, Calif.

[73] Assignee: The Board of Trustees of the Leland Stanford Junior University, Stanford, Calif.

[21] Appl. No.: 125,126

[22] Filed: Feb. 27, 1980

[51] Int. Cl.³ ............................................. G01N 21/00
[52] U.S. Cl. .................................. 356/438; 356/435; 250/343
[58] Field of Search ............... 356/432, 433, 434, 435, 356/436, 437, 438, 301; 250/339, 343

[56] References Cited

U.S. PATENT DOCUMENTS

| | | | |
|---|---|---|---|
| 2,930,893 | 3/1960 | Carpenter et al. | 250/339 |
| 3,146,293 | 8/1964 | Lesage | 356/437 |
| 3,364,351 | 1/1968 | Palmer et al. | 250/343 |
| 3,619,624 | 11/1971 | Sorenson | 356/435 |
| 3,652,850 | 3/1972 | Briggs | 356/343 |
| 3,768,908 | 10/1973 | Zaromb | 356/301 |
| 4,017,193 | 4/1977 | Loiterman | 356/435 |
| 4,228,353 | 10/1980 | Johnson | 250/356 |

FOREIGN PATENT DOCUMENTS 2513061 10/1975 Fed. Rep. of Germany ...... 356/432

*Primary Examiner*—R. A. Rosenberger
*Attorney, Agent, or Firm*—Flehr, Hohbach, Test, Albritton & Herbert

[57] ABSTRACT

The environment within an area is monitored through use of tomographic reconstruction techniques. Signals for use in the tomographic reconstruction are generated optically by a laser which transmits signals to reflectors positioned about the area and then to detectors around or within the area. Several embodiments illustrate the method whereby the signals are generated by sequential illumination of detectors or by simultaneous illumination of detectors.

12 Claims, 4 Drawing Figures

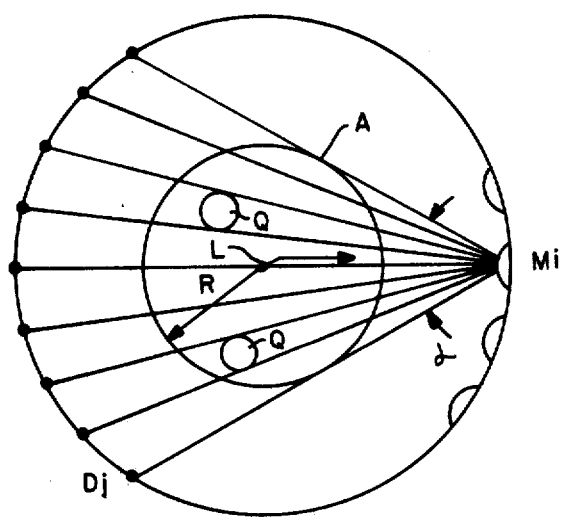
FIG.—1
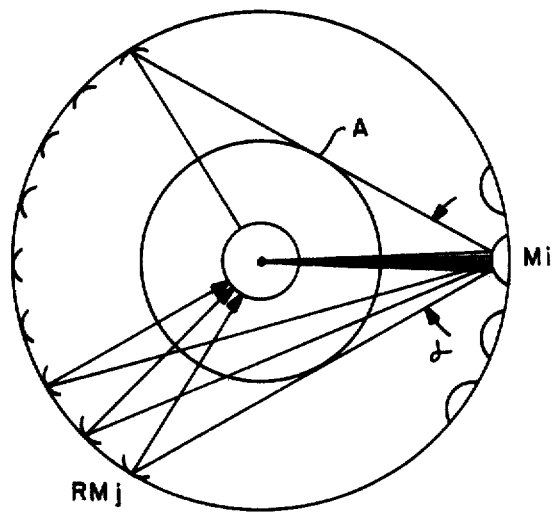
FIG.—2

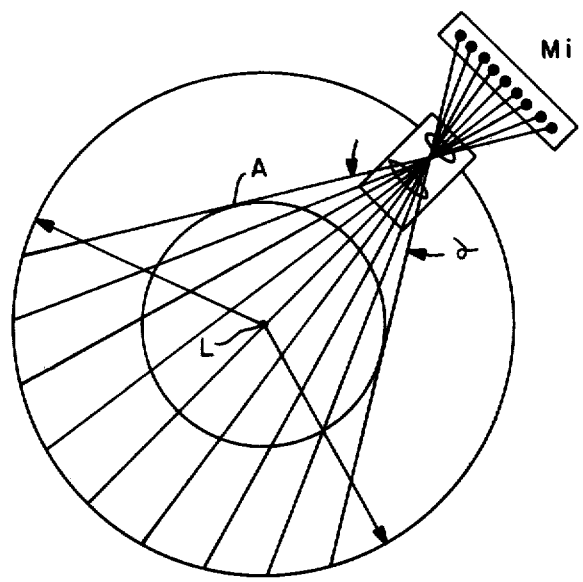
FIG.—3
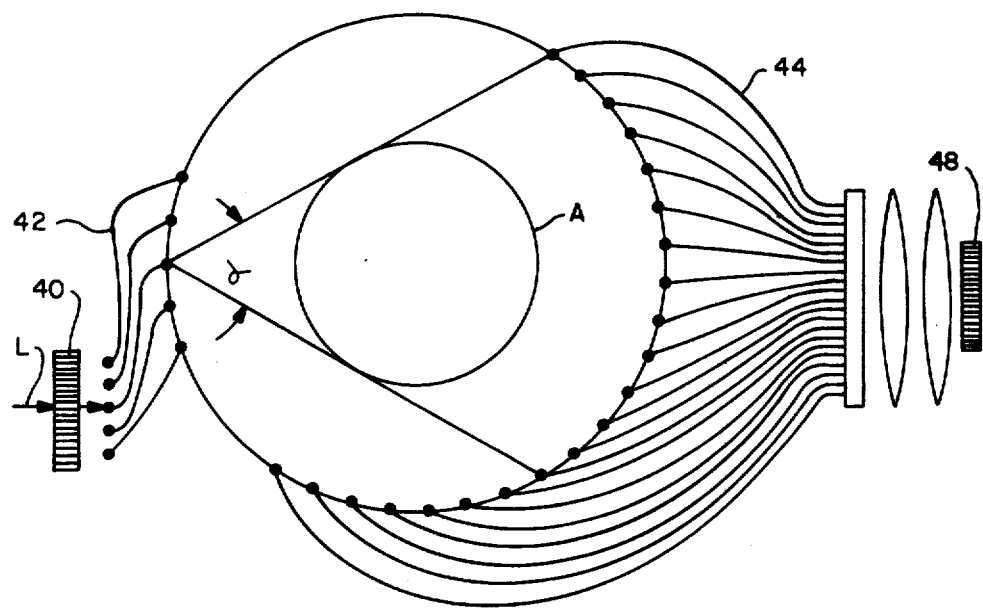
FIG.—4

METHOD AND MEANS FOR OPTICALLY GENERATING SIGNALS FOR USE IN MONITORING AN ENVIRONMENT USING TOMOGRAPHIC TECHNIQUES

This invention relates generally to optically monitoring an environment and more particularly the invention relates to optical methods and means for monitoring an environment through application of tomographic reconstruction techniques.

The use of tunable laser sources for remote pollution measurements is now well known. By applying spectroscopic analysis, the presence of specific gaseous constituents can be identified and quantitatively determined. See for example Patel, "Laser Detection of Pollution", Science, pp. 157–173, 13 October 1978. However, depth resolved absorption measurements using atmospheric back scattering requires high transmitted laser engines in addition to large receiver diameters and high speed detection and signal digitization.

The use of tomographic techniques in medical applications are now well known, also. For example, Hounsfield U.S. Pat. No. 3,778,614 discloses a method of tomographic analysis using an X-ray beam which is transmitted through a body along a plurality of parallel paths in a plurality of scan sets. Boyd, et al, U.S. Pat. No. 4,075,492 discloses a method of radiation tomography wherein the radiation is applied in a fan beam, and a tomograph of the cross section is reconstructed by a process of reordering the received signals from the fan beam. More recently, ultrasonic techniques have been employed in medical tomography. Anderson, U.S. Pat. No. 4,074,564 and Heyser et al, U.S. Pat. No. 3,083,232 disclose reconstruction systems and method for ultrasonic imaging wherein ultrasonic signals are used in place of radiation.

Discussions of the mathematics involved in computerized tomographic reconstructions are given by Shepp and Logan, "The Fourier Reconstruction of a Head Section", IEE Transactions on Nuclear Science, Vol. NS-21, June 1974, pp. 21–43 and by Shepp and Stein in "Simulated Reconstruction Artifacts in Computerized X-Ray Tomography", Reconstruction Tomography in Diagnostic Radiology in Nuclear Medicine, edited by M. M. Ter-Pogossian et al, University Park Press 1977.

The present invention is directed to optical monitoring techniques utilizing tomographic reconstruction techniques, and particularly the invention is related to optical methods and systems for generating the signals needed in tomographic reconstruction.

Accordingly, an object of the present invention is an improved method of monitoring the environment in a defined area.

Another object of the invention is the method of optically generating signals necessary in a computerized tomographic reconstruction of the environment in an area.

Still another object of the invention is means for optically generating signals for the tomographic reconstruction of air pollution within an area.

Briefly, in accordance with one embodiment of the invention an optical system for generating signals indicative of environmental pollution within an area includes a coherent light source such as a laser placed within an area and a plurality of reflectors placed about the area. Light from the source is directed to the reflectors, and the reflected light is received by detection means which generate the electrical signals indicative of optically detectable pollution within the area.

In one embodiment the detectors are positioned about the area in cooperation with the light reflectors whereby light from the source is reflected by each of the reflectors to a plurality of detectors within an angle, gamma, measured from each detector. In this embodiment signals are generated by sequentially illuminating each of the reflectors and detecting the reflected light from each reflector by the plurality of detectors within the angle, gamma.

In another embodiment the plurality of detectors are positioned within the area in close proximity to the light source. The reflectors include a plurality of convex mirrors and a plurality of concave mirrors positioned about the area with the concave mirrors being cooperatively arranged with the convex mirrors whereby light from the source striking a convex mirror is reflected to a plurality of concave mirrors within an angle, gamma, measured from each convex mirror, and the light from the concave mirrors is then reflected to the light detectors. Using this apparatus the signals are generated by sequentially illuminating each convex mirror and detecting the light reflected from the plurality of concave mirrors within the angle gamma.

In still another embodiment the coherent light source is placed within an area and a plurality of detectors and a plurality of light reflectors are positioned about the area. The light reflectors and light detectors are cooperatively arranged whereby light from the source is reflected by a plurality of reflectors with light being received by each light detector from a plurality of reflectors within an angle gamma measured from each detector. Using this apparatus the signals are generated by simultaneously illuminating all of the reflectors and simultaneously detecting the reflected light by all of the detectors.

In yet another embodiment a plurality of light sources are positioned about the area and a plurality of light detector means are positioned about the area. The plurality of light sources may comprise a laser source with optical transmission means selectively interconnecting the laser source to each of the light sources positioned about the area. The light detector means may include a single poly element detector with optical transmission means interconnecting the plurality of light receivers to the poly element detector. In this embodiment the signals are generated by sequentially transmitting light from the laser means to each light source with the light transmitted through the area being received by a plurality of detector means within an angle gamma measured from each light source.

The invention and objects and features thereof will be more fully understood from the following detailed description and appended claims when taken with the drawing, in which:

FIG. 1 is one embodiment of optical means in accordance with the invention for generating signals for monitoring air pollution through use of tomography.

FIGS. 2–4 are alternative embodiments of optical means in accordance with the invention for generating signals for the tomographic reconstruction of air pollution within an area.

Referring now to the drawings, FIG. 1 is a schematic representation of one embodiment of optical means in accordance with the invention. Laser source L is positioned with an area, A, having a radius R in which a plurality of pollutant sources Q are positioned. The area may comprise several square miles and the pollutant sources might be chemical plants and the like which generate industrial effluent. Suitable laser sources are commercially available with the laser power depending on the size of the monitored area. Laser frequency is dependent on the absorption characteristics of the pollution species being monitored.

Positioned about the area are a plurality of reflectors such as convex mirror $M_i$ and a plurality of detectors such as detector $D_j$. The mirrors may be cylindrical with a radius whereby incident light is reflected as a fan beam to a plurality of detectors within the angle gamma. In this embodiment the laser beam is easily rotated and directed towards each reflector on the circumference of the circle. Thus, at each of n points equally spaced on the circumference a reflector such as a cylindrical mirror $M_i$ (i = 1 - - - N) is mounted whereby the collimated incident laser beam is reflected in a fan beam over an angle, gamma, across the circle. The beams from $M_i$ traverse the circular region A and strike a set of m fixed detectors $D_j$ (j = 1 - - - M). The mirrors and detectors lie in a common plane P, which may be parallel to the ground at a sufficient height H so that the beams are not obscured by hills, chimneys, or buildings.

In traversing the path from $M_i$ to $K_j$, the laser beams are attenuated exponentially so that $$P_{ij}^r = P_{ij}^o \exp[-\int_{L_{ij}} \alpha_A(x,y,\lambda)ds],$$

where $P_{ij}^r$ and $P_{ij}^o$ are the received and transmitted powers over the path $L_{ij}$ and $\alpha_A$ $(x,y,\lambda) = \alpha_R(x,y) + \alpha_M(x,y) + \alpha_{abs}(x,y,\lambda)$ is the atmosphere extinction coefficient composed of terms due to Rayleigh and Mie scattering and to molecular absorption. For molecular density N with absorption cross section $\sigma$, $\alpha_{abs}(x,y,\lambda) = N(x,y) \cdot \sigma(\lambda)$.

Projection number $P_{ij}$ is defined to be used as input to the tomographic reconstruction algorithm as the ratio ln $(P_{ij}^o/P_{ij}^r)$, where $P_{ij}^o$ is the normalized intensity at mirror $M_i$. Thus $$P_{ij} = \int_{L_{ij}} \alpha_A(x,y,\lambda)ds. \quad (1)$$

where the integral is over the path from $M_i$ to $D_j$.

To make a measurement, the tunable-laser beam rotates and strikes mirrors $M_i$, which illuminate detectors $D_j$. The projection numbers $P_{ij}$ are measured, stored, and used to form the input to the mathematical algorithm, which allows the approximate reconstruction of $\alpha_A(x,y,\lambda)$ for all (x,y) in the monitored area A. To recover the pollutant density, two successive measurements are made with the laser tuned on and off the pollutant absorption, and the difference in extinction coefficient is taken to yield $N(x,y)\sigma(\lambda)$. The reconstructed pollution field is then gray coded and displayed as a picture.

If $\alpha_A(s,y,)$ is a continuous function f, the Radon theorem guarantees that an exact reconstruction of $\alpha_A(x,y,\lambda)$ can be found, given all projection numbers. In practice, only a finite number of measurements can be made, and an approximation of $\tilde{\alpha}_A(x,y,\lambda)$ to $\alpha_A(x,y,\lambda)$ is formed. The closeness of the approximation of $\tilde{\alpha}_A(x,y,\lambda)$ to $\alpha_A(x,y,\lambda)$ depends on the smoothness of f and on the sampling numbers n and m.

Simulations made for the problem of designing an x-ray tomographic device for human-body sections involved the use of superpositions of several ellipses to simulate body parts. These simulations should also serve well for the air-pollution case because, if Q is a source of pollutant, say a chimney or leak, then by the time the pollutant has attained a height h in the measurement plane, the pollutant source cloud has assumed a circular shape because of diffusion; if there is a wind field, the cloud has assumed an elliptical shape.

Based on the simulations and on Nyquist's theorem, it is a useful rule of thumb that, to detect clearly a circular pollutant cloud, which may be only a few percent more absorbing than the surrounding air, it is necessary that at least two or three line integrals from each fan of measurement cross the cloud. Thus, assuming that the two rays adjacent to the central ray are just tangent to a circular pollutant cloud of radius r = 10 m, where the circle A has radius R = 1000 m, then $m \sim 2\pi/2\sin^{-1}(10/1000) = 314$ detectors are needed. Since for this application the mirrors $M_i$ are mounted on poles or buildings and it is natural to mount the detectors adjacent to $M_i$, we take n = m.

The required transmitted laser power needed to carry out the tomographic measurement can be estimated by setting the power received at the detector equal to the minimum detectable power at a given signal-to-noise ratio. Conservation of energy gives the following expression for the power received at detector $D_j$:

$$P_j^r = KP_i^o \frac{\sqrt{A}}{\pi L_{ij}} \exp[-\int_{L_{ij}} \alpha_A(x,y,\lambda)ds], \quad (2)$$

where K is the system's optical efficiency, $P_i^o$ and $P_j^r$ are transmitted and received powers, $\overline{A}$ is the receiver aperture area, and $L_{ij}$ is the path length. It is assumed that mirror $M_i$ fans the incident laser beam uniformly over a 180° field in the plane and that the circular receiver aperture is large enough to accept the diffraction-limited laser beam out of the plane. Under these assumptions, the fraction of power collected by the receiver is $A/\pi L_{ij}$.

For a dark-current-limited detector likely to be used in the infrared, the minimum detectable power at a signal-to-noise S/N is $$P_{min}^r = NEP(S/N)\sqrt{2\Delta f}, \quad (3)$$

where $\Delta f$ is the detector or electronics bandwidth and $NEP = \sqrt{a}/D^*$ is the detector noise equivalent power, which is related to the detectivity, $D^*$, by the square root of the detector area a.

By setting $P_j^r = P_{min}^r$, the required transmitted power is determined for the measurement at a given (S/N) level as $$P_j^{req} = \frac{NEP(S/N)\sqrt{2\Delta f}}{K\left(\frac{\sqrt{A}}{\pi L_{ij}}\right)\exp[-\int_{L_{ij}} \alpha_A(x,y,\lambda)ds]}. \quad (4)$$

For a pulsed-laser source, the required transmittal energy is found by multiplying Eq.(4) by $\tau$, the system response time, and assuming that $\Delta f \tau = 2$, to give $$E_j^{req} = \frac{2\sqrt{\tau} \; NEP(S/N)}{K_\pi \left(\frac{\sqrt{A}}{L_{ij}}\right) \exp[-\int_{L_{ij}} \alpha_A(x,y,\lambda)ds]} \quad (5)$$

It will be noted that the required power and energy scale linearly with $L_{ij}$ rather than with $L_{ij}^2$, as in the differential-absorption or topographical target-measurement case. Also, it will be noted that the detector bandwidth can be reduced to lower the cost of the detector and digitizing electronics without increasing the required laser power significantly. Here the simplifying assumption is made that the transmitted power is not significantly depleted when tuned onto the absorption resonance. An extension to the case of significant depletion is straightforward and has been treated previously by Byer and Garbuny, "Pollutant detection by absorption using Mie scattering and topographic targets as retroreflectors," Appl. Opt. 12, 1496–1505 (1973).

As a first example, assume that the measurement is made over a 2-km-diameter area with a 10-m depth resolution at $S/N=1000$, $K=0.1$, and $\exp-L_{ij} \alpha_A(x,y,\lambda)ds=e^{-1}$. If a time t is taken to rotate the laser beam and make the measurement, then a mirror $M_i$ is illuminated for a time $\tau_i = W_m t/(2\pi R)$, where $W_m$ is the mirror width. The detector must operate at a bandwidth $\Delta f = 2/\tau_i$ to resolve the signal. For $t=10$ sec, $R=1$ km, and $W_m=10$ cm, we find that $\Delta f = 1.2 \times 10^4$ Hz. To be conservative, assume inexpensive room-temperature detectors with $NEP = 10^{-11}$ W Hz$^{-\frac{1}{2}}$ operating at $10^4$ Hz bandwidth. The calculated required power and energy from Eqs. (4) and (5) is $P_j^{req} = 3.0$ W (cw source), $E_j^{req} = 0.50$ mJ (pulsed source)

for a 10-cm receiver diameter at a 2-km range. These power and energy levels are well within the range of available laser sources and are well below the megawatt-peak-power and 0.1-J energy levels required for depth-resolved measurements by the differential absorption method. With appropriate hardware of the type now used in advanced medical computerized tomography scanners, the function $\bar{\alpha}_A(x,y,\lambda)$ can be reconstructed in approximately 10 sec, thus permitting a 10-m spatially resolved measurement over an area bounded by a 2-km-diameter circle every 10 sec with the pulsed-laser source operating at 30 pulses/sec.

As a second example, consider a 10-km-radius circle with a spatial resolution of 100 m and a measurement time of 10 sec. The illumination time for each detector is $\tau_i = 1.6 \times 10^{-5}$ sec, so that $\Delta f = 1.2 \times 10^5$ Hz. For a liquid-$N_2$ cooled detector with $NEP = 10^{-12}$ W Hz$^{\frac{1}{2}}$ and $\alpha_A = 0.1$ km$^{-1}$, a value typical in the infrared, then $P^{req} = 25$ W (cw source), $E_j^{req} = 0.4$ mJ (pulse source)

for a receiver diameter of 10 cm at a 20-km range. In this case, the improved detector sensitivity offset the order-of-magnitude increase in range. The required cw source power can be reduced by increasing the receiver aperture or the measurement time.

In the first example, the transmitted laser energy is almost two orders of magnitude below that required for a depth-resolved differential absorption measurement at 1-km range. In the second case, a depth-resolved absorption measurement in the infrared would require over six orders of magnitude more transmitted energy and thus be practically infeasible. These examples illustrate the advantage of the $\sqrt{A}/L_{ij}$ scaling dependence for this measurement method.

FIG. 2 is an alternative embodiment in which the light source L is positioned within the area A, and a plurality of convex mirrors $M_i$ are uniformly positioned about the area A. In addition, a plurality of convex mirrors, $RM_j$, are uniformly positioned about the area A. The concave mirrors are cooperatively arranged with the convex mirrors whereby radiation from source L striking convex mirror $M_i$ is reflected to a plurality of concave mirrors within the angle, gamma, as measured at the convex mirror $M_i$, with radiation reflected from the concave mirrors to the detectors $D_k$ positioned about the light source L. In this embodiment the convex mirrors, $M_i$, are sequentially illuminated, and light readings are obtained by detectors $D_k$ of the light reflected from the concave mirrors $R_{mj}$. In this manner a set of fan beam measurements are obtained whereby a tomographic reconstruction is obtained in a manner as above described.

In the foregoing arrangements mirrors around the perimeter of the area to be monitored are sequentially illuminated. Thus, some delay is introduced in exposing the entire area using all detectors. FIG. 3 is another embodiment of the invention in which the detectors are simultaneously illuminated. In this embodiment the light source L is again positioned within the area A with the pulsed laser source simultaneously illuminating a Lambertion scatterer at the perimeter of the monitored area. The scattered radiation is received by a plurality of polyelement detectors, $M_i$, positioned about the area with each element of a detector viewing one ray of a fan and each polyelement detector defining a complete fan having the angle, gamma. Thus, using this optical scheme and method a tomogram exposure is obtained in only two sequential laser pulses. The first pulse is tuned off the species absorption line and acts to normalize the measurement. The second pulse is tuned on the absorption line so that it measures the integrated optical density from the scatter point along a ray to an element of a detector. Thus, the ability to expose the tomogram in a single layer pulse permits application of the technique where sequential measurements over a period of time are ineffective.

FIG. 4 is a schematic representation of another embodiment of the invention in which a plurality of optical sources L are positioned about the area A and a plurality of detectors D are uniformly positioned about the area A. In this embodiment a single laser source applies a laser beam through an acoustic or galvanometric scanner 40 which can selectively apply the laser beam through an optical transmission line such as a fiber optic 42 to each of the light sources L. Each of the light sources L direct a fan beam of light through the angle gamma, to a plurality of detectors D. The detectors are interconnected through optical transmission means such as optical fibers 44 to a relay and image lens 46 which directs the light to a multiple element detector 48. In this embodiment each of the light sources $L_i$, are sequentially illuminated with the detectors within the angle gamma generating a fan beam signal at the multiple element detector 48. The fan beam signals from all of the light sources are then used to construct a tomogram as above described.

Using the optical systems in accordance with the present invention, using a CW or low power laser source and multiple mirror virtual sources, two dimensional air pollution monitoring using conventional computerized tomography is possible over a wide area. The invention can be utilized in other environments such as for flame diagnostics, shock wave diagnostics, and wind tunnel diagnostics. Thus, while the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. In the monitoring of an environment within an area using tomographic reconstruction techniques, the method comprising the steps of
    (a) placing a coherent light source within said area,
    (b) placing a plurality of light detectors and a plurality of light reflectors about said area, said light reflectors and said light detectors being cooperatively arranged whereby light from said source is reflected by each of said reflectors to a plurality of detectors within an angle,
    (c) sequentially illuminating each of said reflectors by said light source,
    (d) detecting light by a plurality of detectors for each of said sequential illuminations and generating electrical signals from the detected light, and
    (e) tomographically reconstructing an image of said environment from said signals.

2. The method as defined by claim 1 wherein said coherent light source comprises a laser source.

3. The method as defined by claim 2 wherein each of said reflectors comprises a convex mirror.

4. The method as defined by claim 2 wherein each of said reflectors comprises a Lambertian scatterer.

5. In the monitoring of an environment within an area using tomographic reconstruction techniques, the method comprising the steps of
    (a) placing a coherent light source within said area,
    (b) placing a plurality of light detectors within said area and in close proximity to said light source,
    (c) placing a plurality of convex mirrors and a plurality of concave mirrors about said area, said concave mirrors being cooperatively arranged with said convex mirrors whereby light from said source striking a convex mirror is reflected to a plurality of concave mirrors within a defined angle and then reflected to said light detectors,
    (d) sequentially illuminating each of said convex reflectors by said light source,
    (e) detecting light for each illumination and generating electrical signals from the detected light, and
    (f) tomographically reconstructing an image of said environment from said signals.

6. The method as defined in claim 5 wherein said plurality of detectors are spaced about said coherent light source.

7. In the monitoring of an environment within an area using tomographic reconstruction techniques, the method comprising the steps of
    (a) placing a coherent light source within said area,
    (b) placing a plurality of light detectors and a light reflector means about said area, said light reflector means and said light detectors being cooperatively arranged wherein light from said source is received by the light detector for said light reflector means within a defined angle measured from said detector,
    (c) simultaneously illuminating said light reflector means,
    (d) detecting reflected light by all of said reflectors and generating electrical signals from the detected light, and
    (e) tomographically reconstructing an image of said environment from said signals.

8. The method as defined by claim 7 wherein each detector includes lens means for imaging reflected light on said detector.

9. The method as defined by claim 8 wherein each detector includes a plurality of detector elements.

10. In the monitoring of an environment within an area using tomographic reconstruction techniques, the method comprising the steps of
    (a) placing a plurality of light source means about said area,
    (b) placing a plurality of light detectors about said area,
    (c) sequentially energizing each light source means,
    (d) detecting light from each of said light source means by a plurality of detectors within an angle measured from each of said light source means and generating electrical signals from the detected light, and
    (e) tomographically reconstructing an image of said environment from said signals.

11. The method as defined by claim 10 wherein said plurality of light source and optical transmission means connecting said light source to each of said plurality of light source means.

12. The method as defined by claim 10 wherein said plurality of light detectors includes a multiple element detector, a plurality of light receivers, and optical transmission means interconnecting said multiple element detector to said plurality of light receivers.

* * * * *